United States Patent [19]
Nelson

[11] Patent Number: 5,481,764
[45] Date of Patent: Jan. 9, 1996

[54] UNDERWATER SEAT RESTRAINT APPARATUS

[76] Inventor: Robert K. Nelson, 2025 E. Timberhill Pl., Springfield, Mo. 65804

[21] Appl. No.: 267,882

[22] Filed: Jun. 28, 1994

[51] Int. Cl.6 .................................................... A47K 3/00
[52] U.S. Cl. ................................................. 4/559; 4/571.1
[58] Field of Search .................................. 4/571.1, 572.1, 4/578.1, 559, 579, 496, 504; 248/205.5, 205.6, 205.7, 205.8, 205.9, 206.2, 206.3; 297/464, 466, 468, 485; 128/870, 876, 877, 878, 882; 292/288

[56] References Cited

U.S. PATENT DOCUMENTS

| | | | |
|---|---|---|---|
| D. 289,793 | 5/1987 | Blake | D23/309 |
| 2,468,742 | 3/1949 | Faulhaber | 4/572.1 X |
| 2,639,852 | 5/1953 | Sanders et al. | 297/485 |
| 3,589,760 | 6/1971 | Williams | 292/288 X |
| 4,637,622 | 1/1987 | Bargard | 297/485 X |
| 4,666,194 | 5/1987 | Charman | 292/288 |

*Primary Examiner*—Charles E. Philips
*Attorney, Agent, or Firm*—Hovey, Williams, Timmons & Collins

[57] ABSTRACT

An apparatus for use in restraining movement of a bather within a bath or spa includes a seat belt including a pair of elongated, pliable straps, and a pair of suction cups for attaching a first end of each strap to a support surface of the bath or spa. A buckle is also provided for fastening the straps together at a point intermediate the first and second ends of each strap.

Release clips may also be provided for releasably connecting the suction cups to the straps so that the straps may be released from connection with the suction cups by manipulation of either the buckle or the clips.

5 Claims, 1 Drawing Sheet

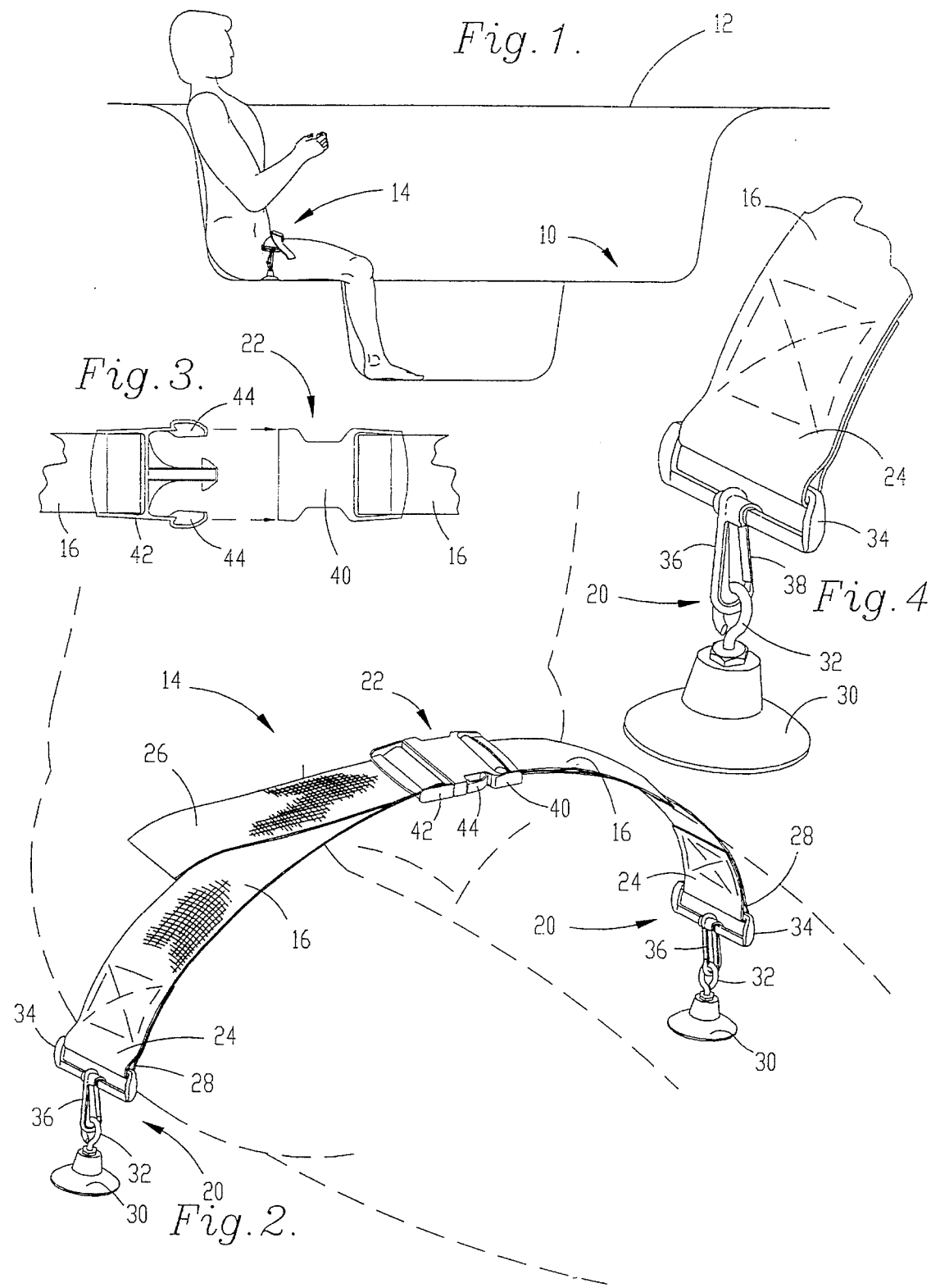

5,481,764

UNDERWATER SEAT RESTRAINT APPARATUS

BACKGROUND OF THE INVENTION

1. Field of the Invention

The present invention relates generally to therapeutic bath or spa accessories and, more particularly, to a restraint apparatus for use in restraining movement and buoyancy of a bather within such a bath or spa.

2. Discussion of the Prior Art

The use of therapeutic baths and spas for public bathing, relaxation, recreation, therapy, or as a social center in homes, clubs and resorts, continues to gain acceptance as such baths and spas become more affordable and easier to maintain and clean.

A common type of therapeutic bath or spa is formed of a unitary shell usually made of cast acrylic or thermal plastic that is secured in a desired location and connected to any necessary plumbing, including air and water sources. Alternately, baths and spas are custom built, and include tile along the exposed walls and seat of the bath or spa. It is also known to provide mobile baths which are formed of stainless steel or the like and mounted on rollers.

In each of these known types of baths and spas, a seat or other support surface is provided for accommodating one or more bathers. Typically, this support surface is positioned at a height in the bath or spa which permits the bather to sit on the surface while being submerged in the water up to about the level of their chest or neck. In addition, one or more water or air jets are provided for delivering pressurized water or air to the bath and circulating the water in the bath. In this manner, the circulating water and air pushes and pulls against the bather's body, from the neck or chest down, providing a therapeutic massage.

One object of many new bath and spa designs is to improve circulation to provide a more vigorous massaging action. However, as fluid forces within a bath or spa increase, the likelihood arises that bathers will be pushed around within the bath or spa, creating an annoyance. This effect is often amplified as to female bathers, who commonly exhibit greater buoyancy than men.

OBJECTS AND SUMMARY OF THE INVENTION

It is an object of the present invention to provide a simple, inexpensive restraint aid that enables bathers to enjoy a therapeutic bath or spa without needing to fight against the currents circulating in the bath or spa. In this manner, bathers are able to enjoy the bath or spa and obtain a relaxing massage.

In accordance with these and other objects evident from the following description of a preferred embodiment of the invention, a seat restraint apparatus is provided for use in restraining movement of a bather within a bath or spa, wherein the bath or spa includes a support surface that is normally submerged during use. The apparatus includes a seat belt including a pair of elongated, pliable straps, and an attachment means for attaching a first axial end of each strap to the support surface. The attachment means includes a pair of suction cups, each connected to the first end of one of the straps. The apparatus also includes a fastening means for fastening the straps together at a point intermediate the first and second ends of each strap.

By providing a restraint apparatus constructed in accordance with the present invention, numerous advantages are realized. For example, by providing an apparatus having a two-piece belt and a suction cup for securing each belt piece to the support surface of a bath or spa, a simple, lightweight construction results which is easy for the bather to carry to and from the bath or spa, and to store in a small duffel bag.

It is also preferred that the apparatus include a release means for releasably connecting the suction cups to the straps so that the straps may be released from connection with the suction cups by manipulation of either the fastening means or the release means. Thus, it is easy for the bather or others to quickly release the hold of the restraint apparatus at any of three locations along the belt.

BRIEF DESCRIPTION OF THE DRAWING FIGURES

A preferred embodiment of the present invention is described in detail below with reference to the attached drawing figures, wherein:

FIG. 1 is a side elevational view of a therapeutic bath or spa, illustrating a restraint apparatus constructed in accordance with the preferred embodiment;

FIG. 2 is a perspective view of the apparatus, illustrating a buckle in the closed position;

FIG. 3 is a plan view of the buckle in an open position; and

FIG. 4 is a fragmentary perspective view of selected elements of the preferred embodiment.

DETAILED DESCRIPTION OF THE PREFERRED EMBODIMENT

A therapeutic bath or spa is illustrated in FIG. 1, and generally includes a floor and a side wall in which a seat or other support surface 10 is provided. The bath or spa is adapted to be filled with water to a level indicated by the line 12, and typically will include several water jets for delivering pressurized water to the bath or spa, and a number of air jets for introducing air into the water.

A bather is also shown in FIG. 1, as is an apparatus 14 for use in restraining movement of the bather from the seat or support surface. The apparatus 14 is illustrated in more detail in FIG. 2, and includes a belt formed of two separate straps 16 an attachment means 20 for attaching an end of each strap to the support surface 10, and a fastening means 22 for fastening the straps together at a point intermediate the ends of each strap.

Each strap 16 of the belt is identical to the other, and is formed of an elongated piece of pliant, water-resistant material, such as nylon or the like. Each strap includes first and second axial ends, wherein the first end 24 is folded over onto itself and stitched together to present a loop 28, and the second end 26 is free. The overall length of the two straps is selected to reach across the lap of the bather, and is preferably even longer in order to accommodate larger persons.

The attachment means 20 includes a pair of suction cups 30, each connected to the first end 24 of one of the straps. As shown in FIG. 4, each suction cup is formed of a resilient, compressible material such as rubber or the like, and is provided with an eye 32 by which the cup is attached to the strap. A link 34 formed of water-resistant material, such as a thermoplastic material or the like, is retained in the loop 28 of each strap 16, and supports a clip 36 by which each suction cup is held. These clips 36 are also formed of a water-resistant material, such as a thermoplastic material or the like, and include spring-biased closure members 38 which can be depressed to release the clips from the suction cups. Thus, the clips define a release means for releasably connecting the suction cups to the straps so that the straps may be released from connection with the suction cups by manipulation of either the fastening means or the clips.

As illustrated in FIG. 3, the fastening means 22 preferably includes a buckle having a pair of buckle members 40, 42, each supported on one of the straps 16. The buckle member 40 is a receptacle having a hollow interior space which opens up both to the sides of the receptacle and to the end of the receptacle facing the other member 42. The member 40 also includes a loop through which the free end of one of the straps 16 may be threaded so that the member is retained on the strap, but may be adjusted along the length of the strap.

The other member 42 also includes a loop through which the free end of the other strap 16 may be threaded so that the member 42 is retained on the strap, but may be adjusted along the length of the strap. In addition, the member 42 includes a pair of resilient, spring-biased fingers 44 which are adapted to protrude through the side openings of the receptacle when the member 42 is inserted into the member 40. The fingers 44 lock the members 40, 42 together when the buckle is in the closed position, as illustrated in FIG. 2, and may be pressed inward of the side openings to permit opening of the buckle. Preferably, both buckle members are formed of a water-resistant material, such as a thermoplastic material or the like.

Alternately, it is possible to employ a fastening means including a rigid loop on one of the straps, and hook and loop materials on the other strap. By providing this construction, it is possible to pull the strap with the hook and loop materials through the rigid loop, and then connect the hook and loop materials together to hold the two straps together.

To use the apparatus, a bather simply enters the bath or spa, takes a seat on the support surface 10, and presses one of the suction cups 30 against the support surface on either side of their body. Thereafter, the bather pulls the straps 16 over their lap and closes the buckle members 40, 42. If the strap is too long to restrain movement of the bather from the support surface, the free ends of the straps may be pulled to adjust the overall length of the belt, and to tighten the belt against the bather.

When the bath or spa is completed, the bather simply unbuckles the members 40, 42 from one another and unseats the suction cups so that he or she can get out of the bath or spa and remove the apparatus. Alternately, the belt may be released by unclipping either of the cups from the belt.

Although the invention has been described with reference to the preferred embodiment illustrated in the attached drawing figures, it is noted that substitutions may be made and equivalents employed herein without departing from the scope of the invention as recited in the claims.

What is claimed is:

1. A seat restraint apparatus for use in restraining movement of a bather within a bath or spa, wherein the bath or spa includes a support surface that is normally submerged in water during use, the apparatus comprising:

a seat belt including a pair of elongated, pliable straps, each having opposed first and second axial ends;

a buckle for fastening the straps together at a point intermediate the first and second ends of each strap, the buckle including a pair of buckle members, one member of said pair of buckle members being supported on each of the straps;

an attachment means for attaching the first axial end of each strap to the support surface, the attachment means including a pair of suction cups, one of said pair connected to the first end of each one of the straps by one of a pair of clips, and each clip releasably connecting a suction cup to a strap so that it is possible to release the bather from the support surface by disconnection of said buckle members or disconnection of one of the clips from a respective suction cup.

2. An apparatus as recited in claim 1, wherein the suction cups are formed of rubber or the like.

3. An apparatus as recited in claim 1, wherein the position of each buckle member is adjustable along the length of the strap on which it is supported.

4. An apparatus as recited in claim 1, wherein the straps are formed of a nylon or water resistant material.

5. An apparatus as recited in claim 1, wherein the buckle is formed of a thermoplastic resin.

\* \* \* \* \*